(12) United States Patent
Uthemann et al.

(10) Patent No.: US 7,967,963 B2
(45) Date of Patent: Jun. 28, 2011

(54) WASTEWATER ANALYSIS SENSOR CARTRIDGE

(75) Inventors: Rolf Uthemann, Köln (DE); Andreas Golitz, Moers (DE); John R. Woodward, Windsor, CO (US)

(73) Assignee: Hach Lange GmbH, Berlin (DE)

( * ) Notice: Subject to any disclaimer, the term of this patent is extended or adjusted under 35 U.S.C. 154(b) by 679 days.

(21) Appl. No.: 11/910,866

(22) PCT Filed: Mar. 30, 2006

(86) PCT No.: PCT/EP2006/061204
§ 371 (c)(1),
(2), (4) Date: Jun. 18, 2008

(87) PCT Pub. No.: WO2006/106071
PCT Pub. Date: Oct. 12, 2006

(65) Prior Publication Data
US 2008/0264788 A1    Oct. 30, 2008

(30) Foreign Application Priority Data
Apr. 8, 2005    (EP) .................................... 05120787

(51) Int. Cl.
*G01N 27/333*    (2006.01)
(52) U.S. Cl. ........ 204/416; 204/417; 204/418; 204/419; 204/433; 204/435
(58) Field of Classification Search .......... 204/400–402, 204/409, 415–420, 433, 435; 205/787.5, 205/789, 789.5, 793
See application file for complete search history.

(56) References Cited

U.S. PATENT DOCUMENTS

| 4,495,050 | A | * | 1/1985 | Ross, Jr. ......................... 204/408 |
| 4,657,657 | A |   | 4/1987 | Stellmacher |
| 6,197,172 | B1 | * | 3/2001 | Dicks et al. .................... 204/416 |
| 6,322,680 | B1 | * | 11/2001 | Itsygin .......................... 204/416 |
| 6,427,003 | B1 |   | 7/2002 | Fletcher et al. |

FOREIGN PATENT DOCUMENTS

| CH | 598592 A5 | 5/1978 |
| DE | 8319463.0 U1 | 9/1985 |
| DE | 4234021 A1 | 4/1994 |
| DE | 4406908 A1 | 9/1995 |
| DE | 29508870 U1 | 11/1995 |
| WO | 2006/106071 A1 | 10/2006 |

OTHER PUBLICATIONS

European Search Report issued in the corresponding application EP 1710567A1 (Application No. 05102787) Sep. 28, 2005.
International Search Report (PCT/ISA/210); Issued in the Corresponding Application PCT/EP2006/061204; Completed May 15, 2006 and Mailed May 26, 2006.

* cited by examiner

*Primary Examiner* — Nam X Nguyen
*Assistant Examiner* — Bach T Dinh
(74) *Attorney, Agent, or Firm* — Norman B. Thot

(57) ABSTRACT

A wastewater analysis sensor cartridge (10) according to the invention is intended to be used only once. It has a liquid-tight housing (20), which contains at least one electrochemical sensor element (30, 32) and at least one reference element (56). Furthermore, the housing (20) contains a sensor element electrolyte tank (40,42) and a reference element electrolyte tank (44). The ion-sensitive membranes (31, 33) of the sensor elements (30, 32) and the housing (20) consist of plastic.

14 Claims, 4 Drawing Sheets

WASTEWATER ANALYSIS SENSOR CARTRIDGE

This is a National Phase Application in the United States of International Patent Application No. PCT/EP2006/061204 filed Mar. 30, 2006, which claims priority on European Patent Application No. 05102787.8, filed Apr. 8, 2005. The entire disclosures of the above patent applications are hereby incorporated by reference.

FIELD OF THE INVENTION

The invention refers to a single-use sensor cartridge for the analysis of wastewater having sensor elements with ion-selective membranes.

BACKGROUND OF THE INVENTION

Sensors for the analysis of wastewater in wastewater treatment plants and the like are relatively susceptible to trouble if only because of the hostile measuring environment, i.e. wastewater. Further, electro-chemical sensor elements or reference elements each require a supply of an electrolyte in an electrolyte tank. If the sensor element or the reference element fails or if the electrolyte tank is empty, the relevant sensor or reference element has to be replaced or the respective electrolyte tank has to be filled with electrolyte. In case of malfunction, it is often not easy to determine which sensor or reference element has to be replaced. Replacing individual sensor elements or refilling the electrolyte tank is cumbersome, tedious and costly.

From DE 295 08 870 U1, a sensor arrangement is known that comprises a plurality of pH sensor elements. The housing and the electrolyte tanks are formed by a plurality of coaxially nested glass tubes. The housing, including the electrolyte tanks of glass, is very complex to manufacture, prone to break during handling, and unsuited for sensor elements with ion selective membranes required for measuring other parameters than the pH value.

A sensor cartridge is known from DE 83 19 463 U, wherein the different tanks and housings are formed by different separate components of glass and/or plastics. The sensor cartridge has to be assembled from the components mentioned. Assembly is complex and error-prone. It is difficult and tedious to achieve a fluid-tight sealing of the components made of different materials.

In view of this, it is an object of the invention to simplify or improve the manufacture and the properties of a waste water sensor cartridge having ion-selective membranes.

SUMMARY OF THE INVENTION

This object is achieved, according to the invention, with a single-use sensor cartridge (10) for the analysis of wastewater that includes: (a) an integral housing (20) of plastics material including at least two electro-chemical sensor elements (30, 32) and at least one reference element (56), and (b) two sensor element electrolyte tanks (40, 42) and a reference element electrolyte tank (44), wherein all electrolyte tanks (40, 42, 44) are formed by the integral housing (20), and each electrochemical sensor element (30, 32) has an ion-selective plastics membrane (31, 33) closing the sensor electrolyte tank (40, 42) and being respectively arranged in an opening of the outer wall of the plastics housing (20).

The invention provides a single-use sensor cartridge for the analysis of wastewater. The sensor cartridge comprises an integral fluid-tight housing, preferably made of plastic material. The housing contains at least two electro-chemical sensor elements and at least one reference element. The integral housing further includes two electrolyte tanks for the sensor element and an electrolyte tank for the reference element, accommodating the electrolyte required for the sensor element and the reference element, respectively. If one of the elements is defect or one of the electrolyte tanks is empty, the entire sensor cartridge is replaced with a new sensor cartridge having completely filled electrolyte tanks and including new sensor elements as well as a new reference element. It is not provided that the sensor element or the reference element is replaceable or that an electrolyte tank can be refilled.

The cumbersome search for the defect element and the cumbersome replacement of individual elements can be omitted. The cumbersome refilling of an electrolyte tank can also be avoided. The service life of the sensor elements and of the reference element can be adapted to the volume of the electrolyte tank, if desired. The sensor elements and the reference element need not endure longer than the supply in the electrolyte tanks will last. Depending on the type of element, this offers further potential for saving costs.

The one-piece housing forms the electrolyte tanks. Inside, the housing has a complex structure providing a plurality of closed or closable chambers. In this manner, a plurality of electrolyte tanks can be formed in the housing virtually without additional costs. Such structures can be formed readily and at low cost by plastics injection molding, for example.

The sensor cartridge can be manufactured in large quantities so that the production costs are relatively low. Since only little handling is still required to replace the sensor elements or a reference element and to refill the electrolyte tanks, the maintenance and repair costs for a wastewater analysis installation, in which the sensor cartridge is used, are lower than for conventional wastewater analysis installations.

Each electrochemical sensor element has an ion-selective plastics membrane closing the sensor electrolyte tank and being arranged in an opening of the outer wall and of the plastics housing. By using plastic material, especially PVC, similar materials are used both for the housing and the ion-selective membrane of the sensor element.

An ion-selective plastics membrane is understood both as a plastics membrane into which ion-exchanging substances are incorporated and so-called "solid state" membranes in which rather insoluble inorganic salts are included.

By using similar materials for the membrane on the one hand and the housing on the other hand, a fluid-tight sealing of the border between the membrane and the housing is simplified and more reliable. Among other reasons, this is due to the housing and the membrane having similar expansion coefficients because of their identical or similar material.

Preferably, the ion-selective plastics membranes are in material engagement with the plastics housing. The material engagement may be achieved by so-called cold welding using a solvent-containing adhesive, for example. It is the use of plastic material for both the housing and the ion-selective membrane that allows for such a material and complete fluid-tight connection between the ion-selective membrane and the housing. As an alternative, HF welding or other methods for making a material connection may be used.

According to a preferred embodiment, the housing wall of the housing forms a part of the tank wall of the electrolyte tanks respectively. The tank walls of the electrolyte tanks and the housing wall of the housing overlap at least partly. Thus, a part of the walls can act together as housing wall and tank wall. Thereby, more overall cavity space is obtained inside the housing that may be used for the electrolyte tanks. By overlapping the walls of the electrolyte tanks with each other and/or with the side wall of the housing, the electrolyte tanks can have their tank volume increased while the housing size remains the same.

In a preferred embodiment, the housing is cup-shaped, the sensor element or elements and a voltaic key and, possibly, the temperature sensor being arranged at the bottom of the cup. The cup opening is closed by a separate lid adhered or welded to the cup or connected otherwise thereto in a fluid-tight manner. The cup lid comprises the electrical coupling elements.

Preferably, a fluid-permeable support structure is provided in each opening of the electrolyte tanks, each support structure bearing a membrane of the relevant sensor element. The membrane of the sensor element rests on the outside of the support structure and is supported and borne thereby.

The electro-chemical sensor element may be an ammonia sensor element and/or a potassium sensor element for compensating the cross-sensitivity of the ammonium sensor element.

The reference element may be designed as a pH probe forming a reference arrangement together with the reference electrolyte and a voltaic key.

In a preferred embodiment, the housing has an electro-mechanical coupling arrangement with which it can be coupled to a corresponding electro-mechanical coupling arrangement of a land-side installation. On the one hand, the coupling arrangement serves to mechanically attach the sensor cartridge to the land-side installation, e.g. a holding frame mounted on the land adjacent the wastewater basin and having a corresponding holding arm extending into the clarification basin or into the wastewater. On the other hand, the coupling arrangement serves to electrically connect the sensor element and the reference element to the land-side installation in which the electrical signals from the sensor element and the reference element are evaluated.

In a preferred embodiment, the coupling arrangement comprises a sealing element so that it may be coupled to the coupling arrangement of the land-side installation in a fluid-tight manner. The inside of the coupling arrangements coupled together is insulated from the environment in a fluid-tight manner so that the electric connections between both coupling arrangements are not subjected to humidity or liquid.

Preferably, the housing bears a temperature sensor. A voltaic key element for the reference element, e.g. in the form of a salt bridge, may be borne by the housing.

BRIEF DESCRIPTION OF THE DRAWINGS

The following is a detailed description of an embodiment of the invention with reference to the drawings.

In the figures.

DETAILED DESCRIPTION OF THE INVENTION

Figure 1:
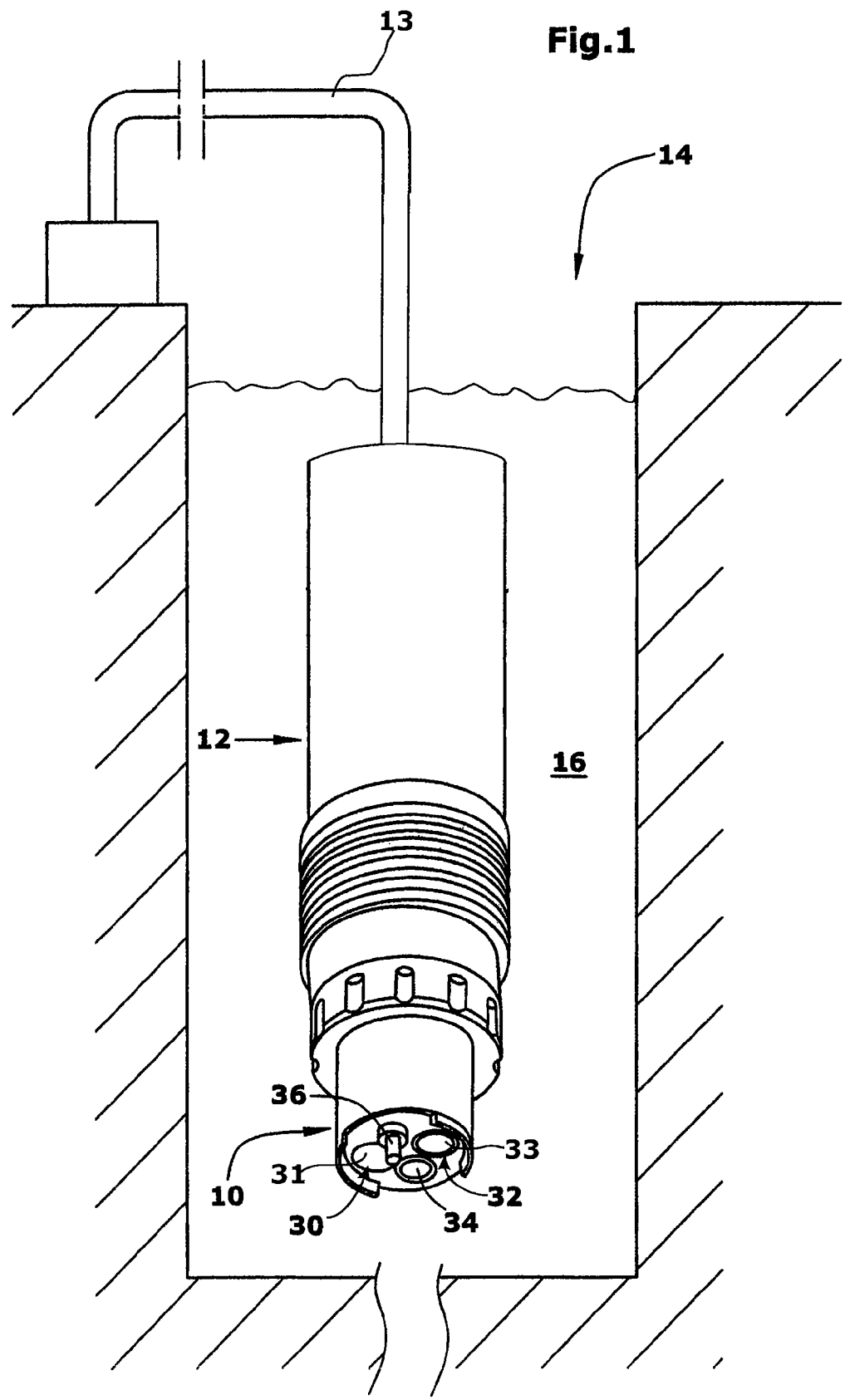
FIG. 1 is an installation for analyzing wastewater comprising a sensor cartridge for the analysis of wastewater according to the present invention.
Figure 2:
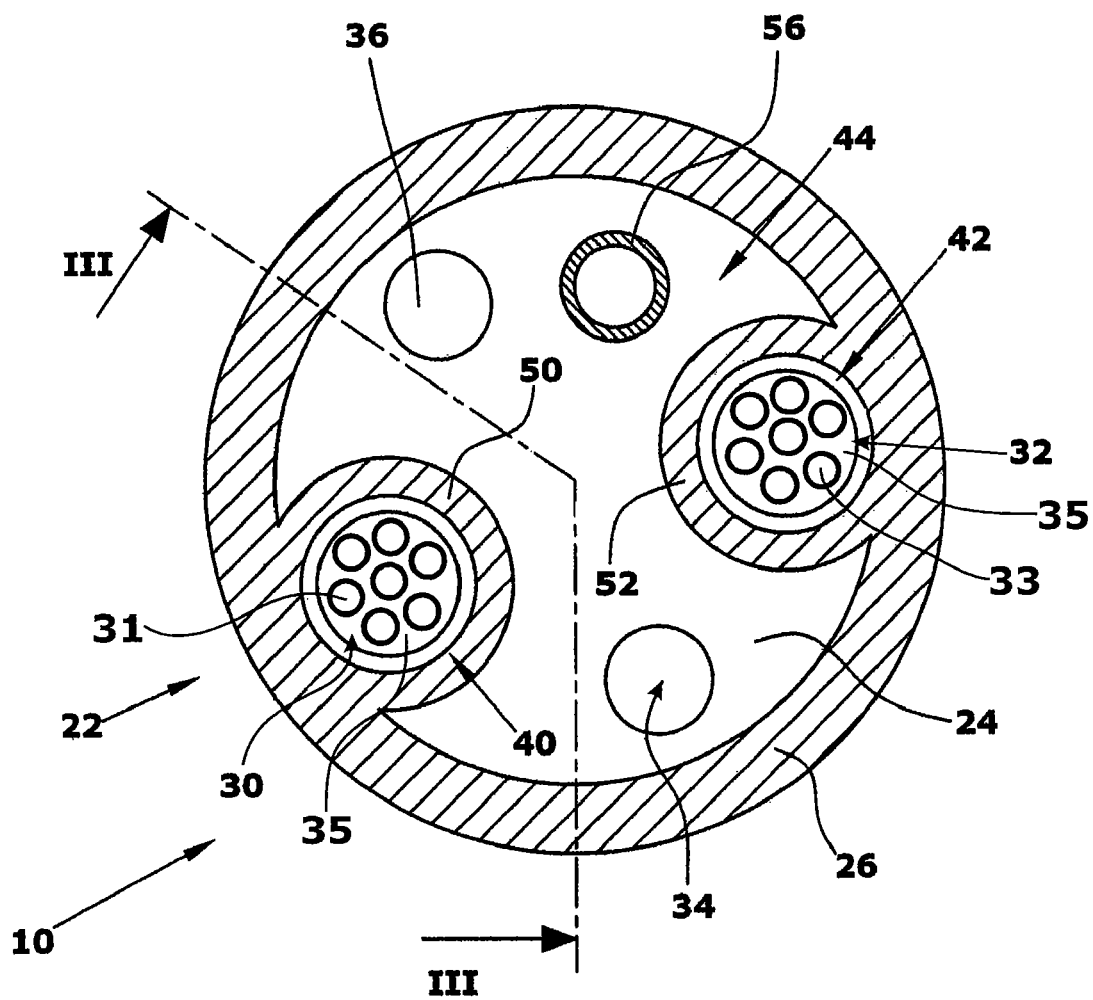
FIG. 2 is a cross sectional view of the sensor cartridge for the analysis of wastewater of FIG. 1.

FIGS. 1 to 5 illustrate a sensor cartridge 10 for the analysis of wastewater removably attached to a holding device 12 mounted on the land. The holding device 12, together with the sensor cartridge 10, is fully immersed into a wastewater basin 14 of a wastewater treatment plant.

The sensor cartridge 10 comprises an integral fluid-tight plastics housing 20 which in turn consists of an integral housing cup 22 with a bottom wall 24, a side wall 26 and a lid wall 28 adhered or welded to the housing cup 22. The housing cup 22 is almost cylindrical in shape. The bottom wall 24 and the side wall 26 form an outer wall of the housing 20.

Two electro-chemical sensor elements 30, 32, a voltaic key element 34 as well as a temperature sensor 36 are arranged in the bottom wall 24 of the cup 22. A rod-shaped reference element 56 protrudes vertically into the housing 20 or the cup 22 from above.

The first electro-chemical sensor element 30 serves to electro-chemically measure ammonia, the second sensor element 32 serves to electro-chemically measure potassium to compensate for the cross sensitivity of the ammonia measurement. The voltaic key element 34 is designed as a so-called salt bridge that serves as a voltage transmitter and comprises a fluid or gel-like electrolyte between two diaphragms. The temperature sensor 36 serves to determine the wastewater temperature.

The two sensor elements 30, 32 and the reference element 56 are each associated with a respective electrolyte tank 40, 42, 44 formed by tank walls 50, 52 in the housing 22. The housing side wall 26 is joined by the two cylindrical tank walls 50, 52 that partly overlap with the housing side wall 26 so that the housing side wall 26 partly forms the tank wall 50 of the two electrolyte tanks 40, 42 that are not otherwise lined. The remaining inner space within the housing 20 and outside the electrolyte tank 40, 42 forms the electrolyte tank 44 of the reference element 56. The overlapping of the housing side wall 26 and the tank walls 50, 52 of the electrolyte tanks 40, 42 allows for a maximum volume of the reference element electrolyte tank 44.

Each electro-chemical sensor element 30, 32 comprises a respective ion-selective plastics membrane 31, 33 closing the relevant sensor electrolyte tank 40, 42 and being arranged in an opening in the outer wall of the housing 20, respectively. The ion-selective plastics membrane 31, 33 is formed by a small plastics plate charged with ionophores that define which ions can penetrate into the membrane 31, 33. Both plastics membranes 31, 33 are materially connected with the plastics housing 20 by cold welding using a solvent-containing adhesive. Thus, an absolutely fluid-tight sealing is obtained. The ion-selective plastics membrane 31, 33 may alternatively also be designed as a "solid state" membrane charged with relatively insoluble inorganic salts.

A respective fluid-permeable support structure 35 is arranged in the opening in which the two ion-selective membranes 31, 33 are seated, the support structure bracing the relevant ion-selective membrane 31, 33 from inside against the liquid pressure. The support structure 35 has rather small openings for achieving fluid-permeability and my be designed as a grid structure or a perforated structure. The support structure 35 is also made of plastics material.

The reference element 56 is designed as a pH probe depending axially from the lid 28 towards the bottom wall 24 of the cup and being immersed in the electrolyte. The reference element 56, the electrolyte in the reference element electrolyte tank 44 and the voltaic key 34 together form a reference arrangement supplying a reference signal for the sensor signals obtained from the two sensor elements 30, 32.

Figure 3:
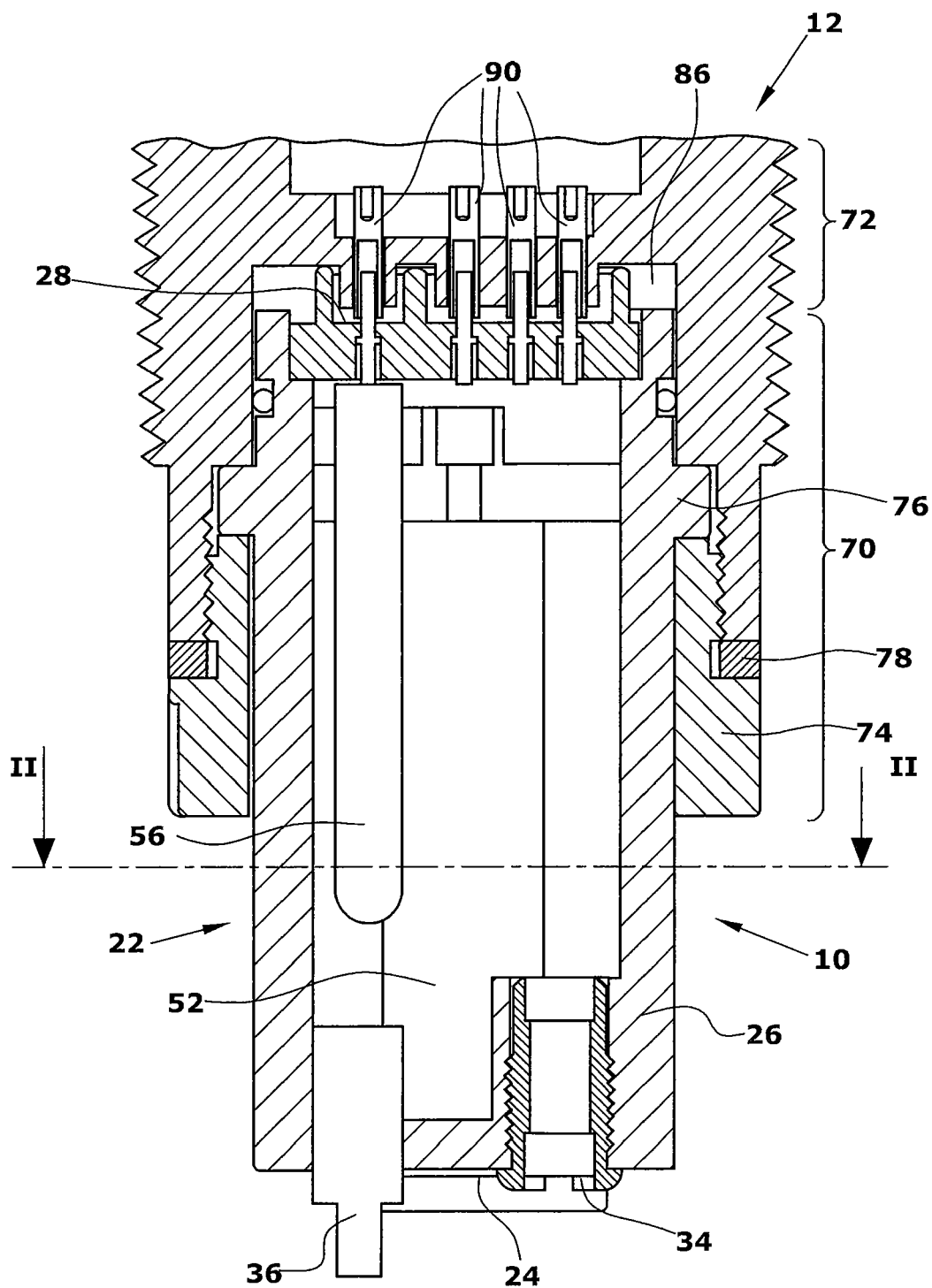
FIG. 3 is a longitudinal section of the sensor cartridge for the analysis of wastewater of FIG. 1.
Figure 4:
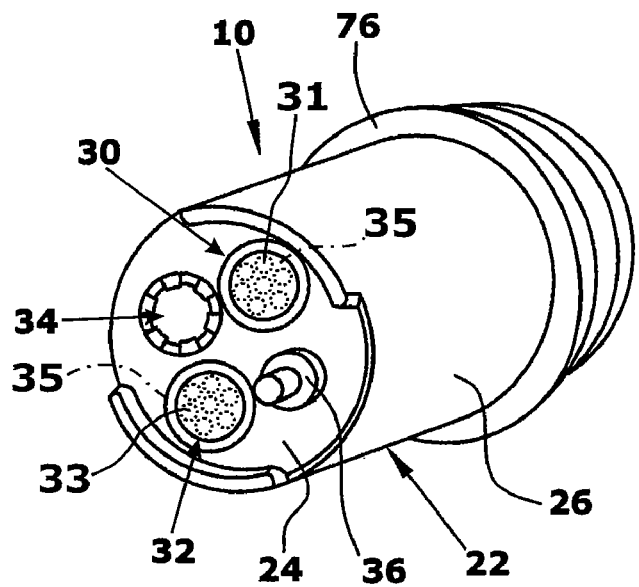
FIG. 4 is a perspective bottom view of the sensor cartridge for the analysis of wastewater of FIG. 1.
Figure 5:
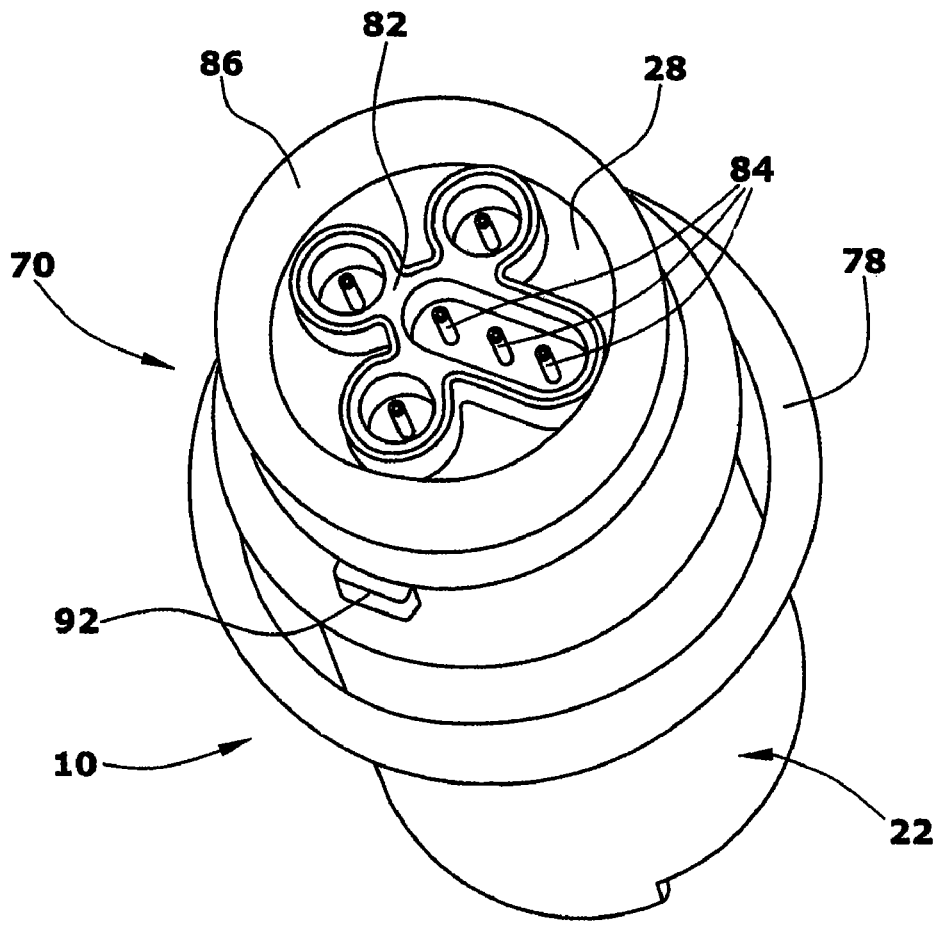
FIG. 5 is a perspective view of the sensor cartridge for the analysis of wastewater of FIGS. 1 to 4, seen from the coupling arrangement side.

The longitudinal end of the housing 20 opposite the cup bottom 24 is provided with an electro-mechanical coupling arrangement 70 that may be coupled to a corresponding electro-mechanical coupling arrangement 72 of the holding device 12, as is illustrated in FIG. 3. The coupling arrangements 70, 72 may be coupled in a fluid-tight manner.

The coupling arrangement 70 of the sensor cartridge 10 substantially comprises a swivel nut 74, a swivel nut flange 76, a swivel nut sealing ring 78, a radial sealing ring 80, as well as contact pins 84 surrounded by contact shielding walls 82 and an end seal ring 86.

The contact pins 84 are plugged into corresponding contact bushings 90 of the coupling arrangement 72 of the holding device 12. Mounting or detaching the sensor cartridge 10 to or from the holding device 12 is effected by correspondingly tightening or loosening the swivel nut 74. Further, as anti-twist devices, two retaining noses 92 are provided at the housing that engage in corresponding recesses in the holding device 12.

The holding device 12 has a liquid-tight housing accommodating the measuring electronics. The proximity of the measuring electronics to the sensor elements and the reference element allow for a reliable and exact evaluation of the relatively weak measuring signals. The holding device may be mounted rigidly and stationarily to a holding tube 13, but it may also be suspended from a cable.

Upon malfunction, upon a calculated immediate and/or signalled depletion of one of the electrolyte tanks, the sensor cartridge 10 to be replaced is pulled off after loosening the swivel nut 74 and a new sensor cartridge 10 is installed by coupling the same and tightening the swivel nut. A time-consuming search for failures, a replacement of individual parts or a tedious manual replenishing of the electrolytes is omitted.

The invention claimed is:

1. A single-use sensor cartridge for the analysis of wastewater comprising:
   a one-piece housing of plastics material including at least two electro-chemical sensor elements and at least one reference element; and
   two sensor element electrolyte tanks and a reference element electrolyte tank, wherein
   all electrolyte tanks are formed by the one-piece housing,
   each electro-chemical sensor element has an ion-selective plastics membrane closing the sensor electrolyte tank and is respectively arranged in an opening of an outer wall of the one-piece housing, and
   a housing side wall forms a part of a wall of each of the electrolyte tanks.

2. The sensor cartridge for the analysis of wastewater of claim 1, wherein each ion-selective plastics membrane is materially connected with the one-piece housing.

3. The sensor cartridge for the analysis of wastewater of claim 2, wherein a fluid-permeable support structure is arranged in an opening of each sensor electrolyte tank, and the support structure bears the plastics membrane of the respective sensor element.

4. The sensor cartridge for the analysis of wastewater of claim 2, wherein a housing side wall partly forms a wall of each of the electrolyte tanks.

5. The sensor cartridge for the analysis of wastewater of claim 2, wherein a housing side wall is cup-shaped, and the sensor elements are arranged on a bottom wall of the cup-shaped housing side wall.

6. The sensor cartridge for the analysis of wastewater of claim 1, wherein a fluid-permeable support structure is arranged in an opening of each sensor electrolyte tank, and the fluid-permeable support structure bears the ion-selective plastics membrane of the respective sensor element.

7. The sensor cartridge for the analysis of wastewater of claim 6, wherein a housing side wall partly forms a wall of each of the electrolyte tanks.

8. The sensor cartridge for the analysis of wastewater of claim 6, wherein a housing side wall is cup-shaped, and the sensor elements are arranged on a bottom wall of the cup-shaped housing side wall.

9. The sensor cartridge for the analysis of wastewater of claim 1, wherein the housing side wall is cup-shaped, and the sensor elements are arranged on a bottom wall of the cup-shaped housing side wall.

10. The sensor cartridge for the analysis of wastewater of claim 1, wherein the one-piece housing comprises an electro-mechanical coupling arrangement with which the sensor cartridge may be coupled to a corresponding electro-mechanical coupling arrangement of a holding device mounted on land.

11. The sensor cartridge for the analysis of wastewater of claim 10, wherein the coupling arrangement of the one-piece housing has a sealing element so that the coupling arrangement of the one-piece housing and the coupling arrangement of the holding device may be coupled with each other in a fluid-tight manner.

12. The sensor cartridge for the analysis of wastewater of claim 1, wherein the one-piece housing bears a temperature sensor.

13. The sensor cartridge for the analysis of wastewater of claim 12, wherein the one-piece housing bears a voltaic key element for a reference element.

14. The sensor cartridge for the analysis of wastewater of claim 1, wherein a housing side wall is cup-shaped, and the sensor elements are arranged on a bottom wall of the cup-shaped housing side wall.

* * * * *